(12) United States Patent
Azapagic et al.

(10) Patent No.: US 11,446,431 B2
(45) Date of Patent: Sep. 20, 2022

(54) INFUSION PUMP APPARATUS HAVING CONVEX PLATEN SURFACE

(71) Applicant: Zevex, Inc., Salt Lake City, UT (US)

(72) Inventors: Azur Azapagic, New Haven, CT (US); Kent F. Beck, Layton, UT (US); J. Ryan Stanfield, Sandy, UT (US)

(73) Assignee: ZEVEX, INC., Salt Lake City, UT (US)

( * ) Notice: Subject to any disclaimer, the term of this patent is extended or adjusted under 35 U.S.C. 154(b) by 182 days.

(21) Appl. No.: 16/683,735

(22) Filed: Nov. 14, 2019

(65) Prior Publication Data
US 2021/0146040 A1 May 20, 2021

(51) Int. Cl.
*A61M 5/142* (2006.01)
*A61M 5/14* (2006.01)

(52) U.S. Cl.
CPC ...... *A61M 5/14228* (2013.01); *A61M 5/1413* (2013.01); *A61M 2205/12* (2013.01)

(58) Field of Classification Search
CPC ............ A61M 5/14228; A61M 5/1413; A61M 2205/12; A61M 2205/121; A61M 5/14232
See application file for complete search history.

(56) References Cited

U.S. PATENT DOCUMENTS

| | | | |
|---|---|---|---|
| 5,078,683 A * | 1/1992 | Sancoff et al. ... | A61M 5/14228 604/67 |
| 5,151,019 A | 9/1992 | Danby et al. | |
| 5,980,490 A * | 11/1999 | Tsoukalis ............. | F04B 43/082 417/474 |
| 6,164,921 A | 12/2000 | Moubayed et al. | |
| 6,267,559 B1 | 7/2001 | Mossman et al. | |
| 8,133,035 B2 | 3/2012 | Wolff | |
| 8,337,168 B2 | 12/2012 | Rotem et al. | |
| 8,777,597 B1 * | 7/2014 | Geschwender ..... | F04B 43/1223 417/475 |
| 9,523,359 B1 * | 12/2016 | Geschwender ......... | F04B 43/12 |
| 2005/0214146 A1 | 9/2005 | Corwin et al. | |
| 2012/0191059 A1 * | 7/2012 | Cummings et al. ........................ | A61M 2205/12 604/500 |

FOREIGN PATENT DOCUMENTS

CN 201461339 U 5/2010
WO 2006/013316 A1 2/2006

* cited by examiner

*Primary Examiner* — Bhisma Mehta
*Assistant Examiner* — John J Crawford
(74) *Attorney, Agent, or Firm* — Hodgson Russ LLP (57) ABSTRACT

A peristaltic infusion pump system has a convex platen surface opposite a linear peristaltic pumping mechanism. The convex platen surface may be part of a cassette of an administration set removably loadable in an infusion pump, or the convex platen surface may be a feature of the pump itself. Pumping efficiency is improved without giving up the ability to have independently controlled compensating fingers. The convex platen surface may have a trapezoidal profile, a curved profile, or a hybrid profile having upstream and downstream inclined portions connected by an intermediate curved portion.

19 Claims, 6 Drawing Sheets

INFUSION PUMP APPARATUS HAVING CONVEX PLATEN SURFACE

FIELD OF THE INVENTION

The present invention relates to peristaltic infusion pumps and cassettes removably loadable therein.

BACKGROUND OF THE INVENTION

Programmable infusion pumps are used to carry out controlled delivery of liquid food for enteral feeding and liquid medications for various purposes such as pain management. In a common arrangement, an infusion pump receives a disposable administration set comprising flexible tubing through which an infusion liquid is pumped. A segment of the administration set tubing may be resiliently deformable and is designed to be engaged by a peristaltic pumping mechanism of the infusion pump. The pumping mechanism may include a series of pumping fingers arranged along the deformable tubing segment. The pumping fingers may be driven cyclically to act upon the tubing segment in a peristaltic manner to force liquid to flow through the tubing in a pumping direction. A platen surface is provided on an opposite side of the tubing segment from the pumping mechanism to brace the tubing segment while the pumping segment is sequentially engaged by the pumping fingers. The platen surface may be part of the pump, for example an inner surface of a door which closes over the tubing segment when the administration set is loaded in the pump. Alternatively, the administration set may include a cassette which is loadable in the pump and through which the tubing segment extends, and the platen surface may be part of the cassette.

In programmable infusion pumps, liquid flow linearity (i.e. constant flow rate) is very important for achieving volumetric accuracy and continuity of liquid flow to the patient. Peristaltic pumping mechanisms have an inherent flaw with respect to flow linearity and continuity because the pumping cycle has a no-flow region and a back-suction region that occur as a locally deformed portion of the tubing segment upstream from a displaced volume of liquid in the tubing segment is allowed to resiliently return to its non-deformed state. This is typically about 30% of the pumping cycle, i.e. 30% of the time there is no flow.

Linear peristaltic infusion pumps are known, for example as disclosed in U.S. Pat. No. 6,267,559. The pumping fingers are arranged parallel to one another along a straight tubing segment, and may be driven independently by respective cams or actuators in a generally sinusoidal fashion. In linear peristaltic pumps, efforts have been made to improve flow linearity by providing an independently actuated compensating finger to reduce the no-flow and back-suction regions of the pumping cycle.

A curvilinear peristaltic infusion pump is known from U.S. Pat. No. 6,164,921. The pump has a single rotatable cam configured to cyclically drive a plurality of pumping fingers in a generally radial direction as the cam rotates. A tubing segment of the administration set is arranged along a curved path between the radial pumping fingers and a concave platen surface provided on a hinged door of the pump. This type of pump provides improved pumping efficiency relative to a linear peristaltic pump because the curved platen surface allows for a longer tubing segment for the same pumping mechanism length such that each pumping finger stroke pumps a greater volume of liquid. However, in curvilinear peristaltic pumps, an independently actuated compensating finger cannot be implemented because the pumping fingers are actuated by the single cam in a radial fashion and therefore cannot be controlled independently.

SUMMARY OF THE INVENTION

The present disclosure describes a peristaltic infusion pump system having a convex platen surface opposite a linear peristaltic pumping mechanism. The convex platen surface may be part of a cassette of an administration set removably loadable in an infusion pump. Alternatively, the convex platen surface may be a feature of the pump itself. According to the disclosure, pumping efficiency is improved without giving up the ability to have independently controlled compensating fingers.

According to one embodiment, a cassette for use with a pump for delivering liquid to a patient comprises a cassette body including a convex platen surface, and a segment of resiliently deformable tubing mounted to the cassette body for conveying a flow of liquid, wherein at least a portion of the tubing segment extends adjacent to the convex platen surface along a non-linear path determined by the convex platen surface. The convex platen surface may have a trapezoidal profile and may include an upstream surface region, a downstream surface region, and an intermediate surface region between the upstream and downstream surface regions, wherein the tubing segment follows the trapezoidal profile of the convex platen surface. The convex platen surface may have a curved profile. The convex platen surface may have a hybrid profile defined by an upstream surface region and a downstream surface region each having an inclined linear profile, and an intermediate surface region connecting the upstream and downstream surface regions and having a curved profile.

According to another embodiment, an infusion pump includes a hinged door for closure over administration set tubing, wherein a convex platen surface is provided on an underside of the pump door. The convex platen surface may have any of a variety of convex profiles summarized above.

BRIEF DESCRIPTION OF THE DRAWINGS

The nature and mode of operation of the present invention will now be more fully described in the following detailed description taken with the accompanying drawing figures, in which.

DETAILED DESCRIPTION OF THE INVENTION

Figure 1:
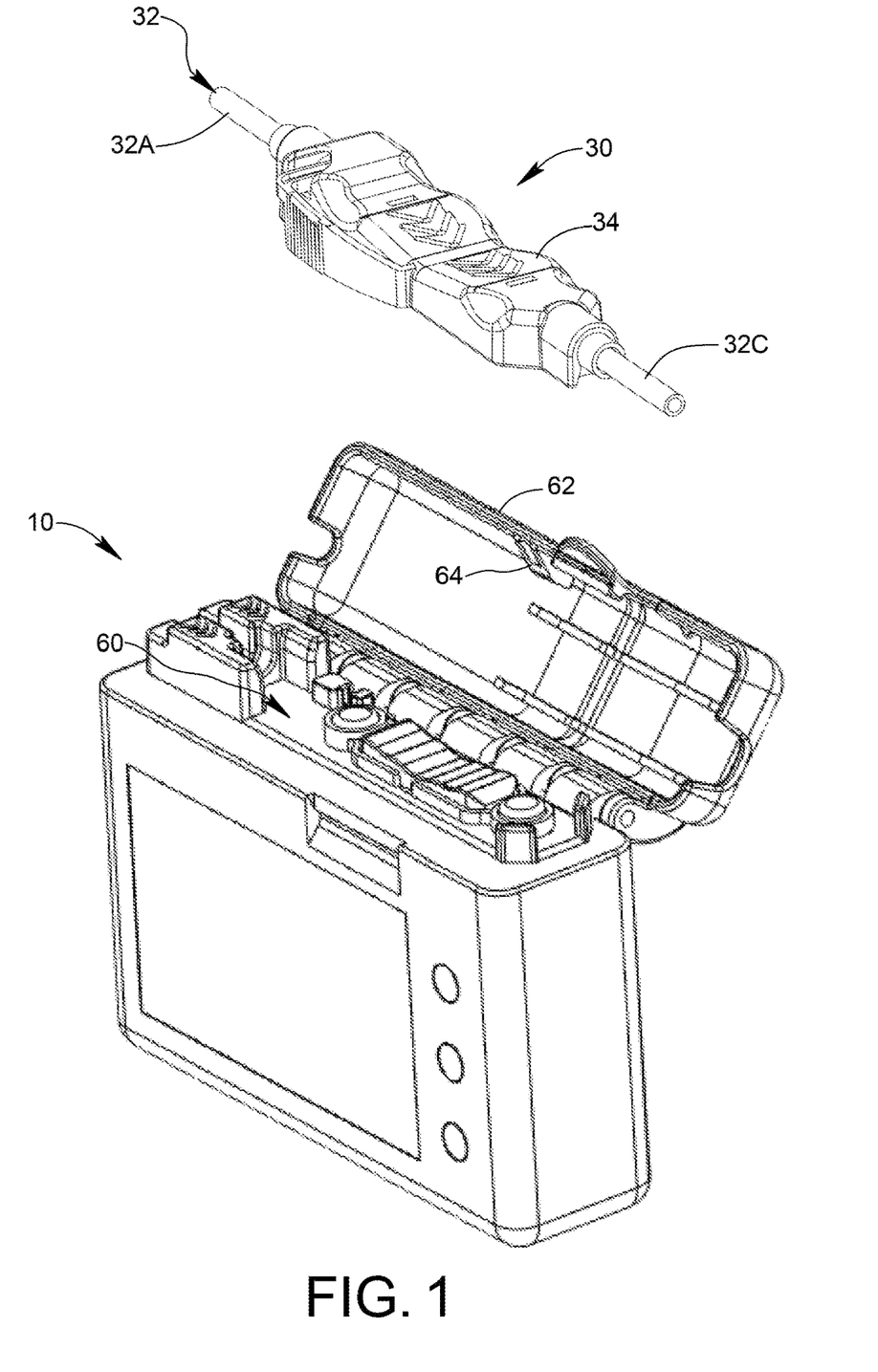
FIG. 1 is an exploded perspective view showing an infusion pump and a portion of an administration set formed in accordance with an embodiment of the present disclosure.
Figure 2:
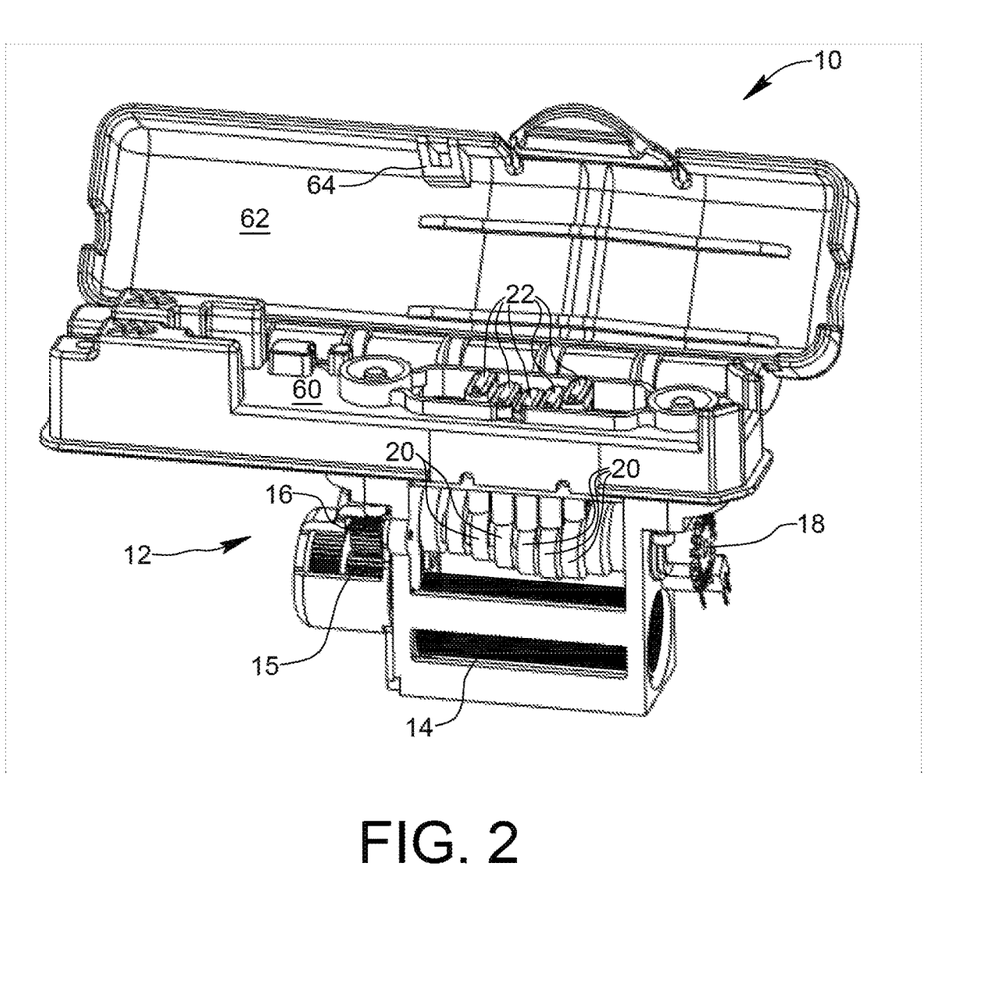
FIG. 2 is a view of the infusion pump shown in FIG. 1 with a housing of the pump removed to reveal internal components of the pump.
Figure 3A:
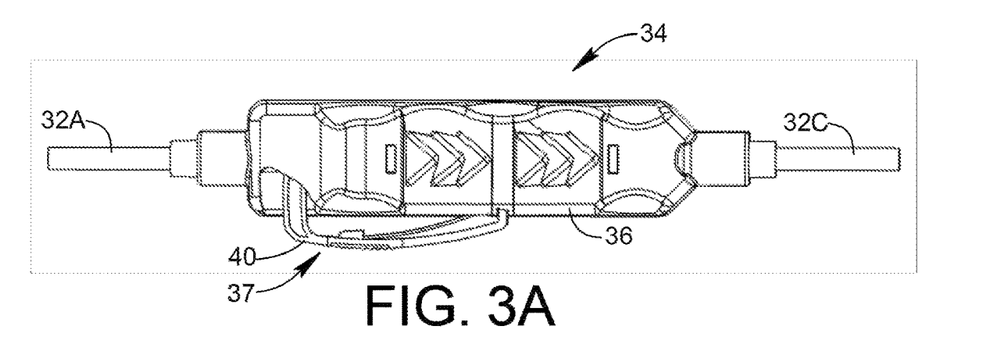
FIG. 3A is a top plan view of a cassette of the administration set shown in FIG. 1, wherein a pinch arm of the cassette is shown in its closed position.
Figure 3B:
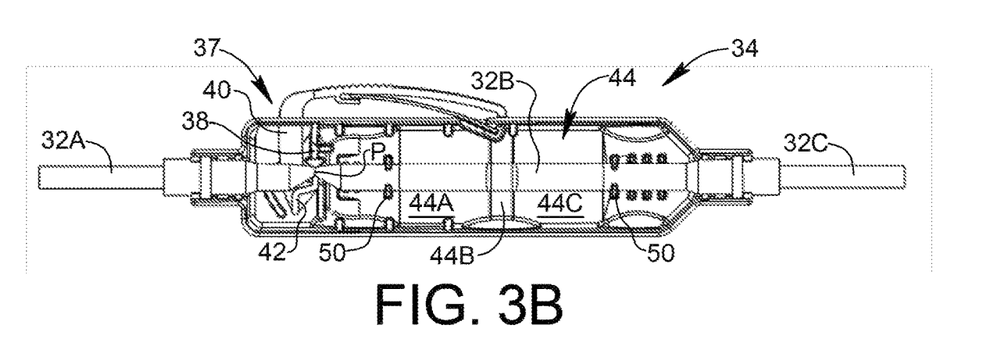
FIG. 3B is a bottom plan view of the cassette shown in FIG. 3A.
Figure 4A:
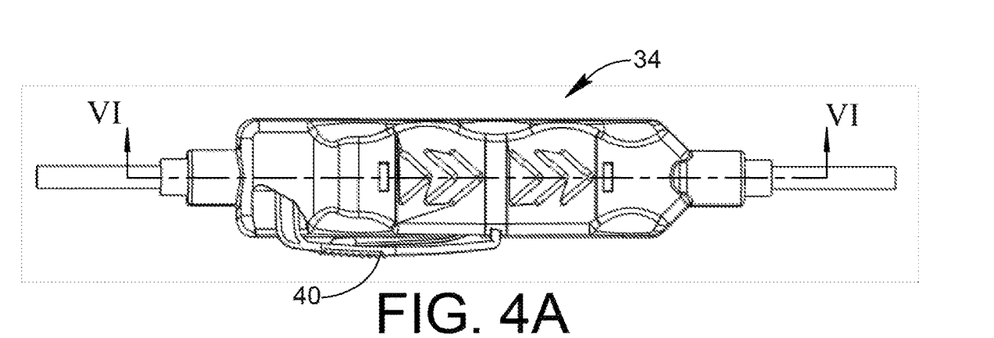
FIG. 4A is another top plan view of the cassette, wherein the pinch arm of the cassette is shown in its open position.
Figure 4B:
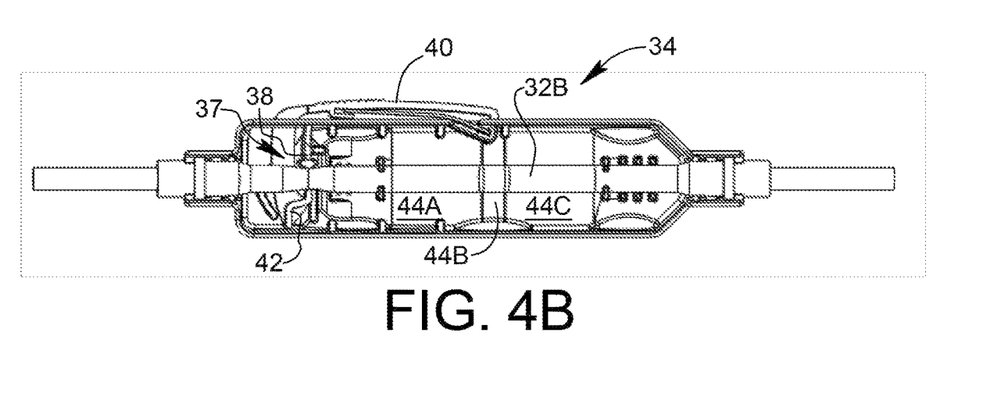
FIG. 4B is a bottom plan view of the cassette shown in FIG. 4A.
Figure 7:
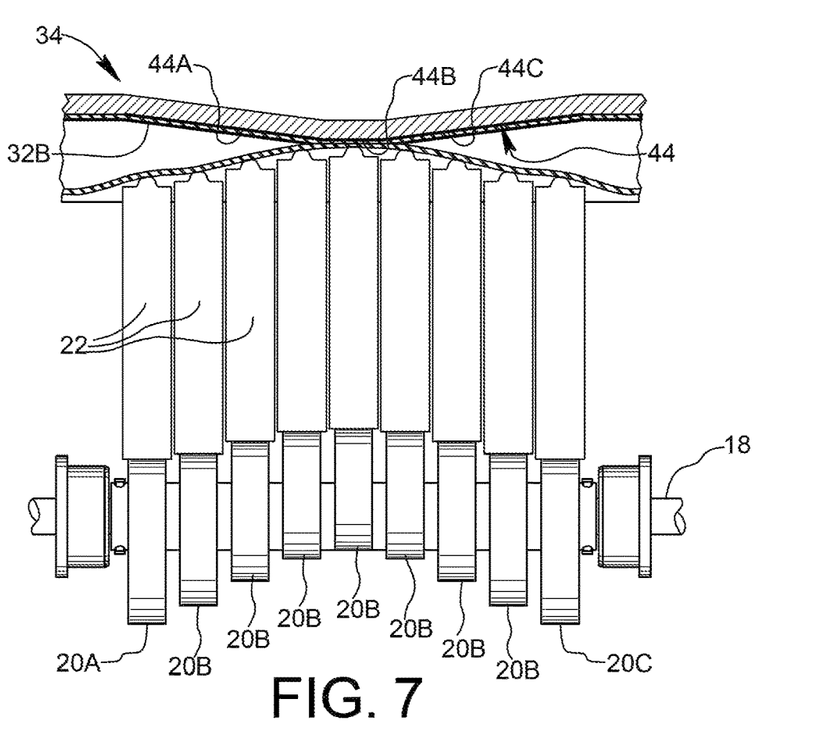
FIG. 7 is a schematic view showing the pumping mechanism with a convex platen surface and tubing segment of the cassette.
Figure 11:
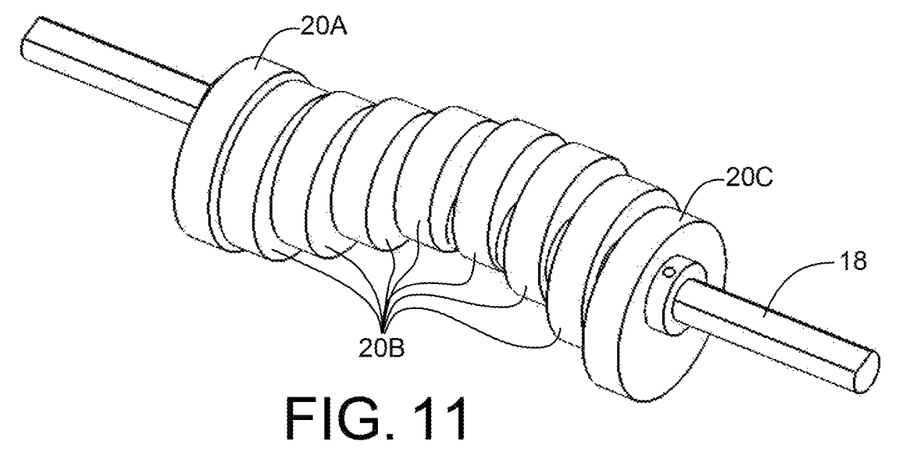
FIG. 11 is a perspective view of a camshaft of the pumping mechanism according to an embodiment of the present disclosure.

FIG. 1 shows an infusion pump 10 and part of a disposable administration set 30 designed to be removably received by infusion pump 10. As seen in FIG. 2, infusion pump 10 includes a pumping mechanism 12 having an electric motor 14 coupled to a drive gear 15 meshed with a driven gear 16 which is fixed to a camshaft 18. A plurality of eccentric cams 20 are mounted on camshaft 18 for rotation with the camshaft, wherein each cam 20 is arranged to engage a respective pumping finger 22. As may be understood, motor 14 is operable to rotate camshaft 18 and cams 20 about the axis of camshaft 18 such that each of the pumping fingers 22 moves radially in a reciprocating fashion away from and toward camshaft 18. Eccentric cams 20 may be configured such that motion of the pumping fingers 22 provides a cyclical peristaltic pumping action along a longitudinal direction of pumping mechanism 12, i.e. in a direction parallel to the axis of camshaft 18. In FIGS. 7 and 11, cams 20 are labelled to distinguish a pair of end cams 20A, 20C from intermediate cams 20B located between the pair of end cams 20A, 20C.

As shown in FIG. 1, administration set 30 comprises tubing 32 for conveying an infusion liquid, and a cassette 34 loadable into infusion pump 10. Cassette 34 is also shown in FIGS. 3A, 3B, 4A, and 4B. Tubing 32 may include a resiliently deformable tubing segment 32B which may be provided as part of cassette 34 and is intended to be operatively engaged by pumping mechanism 12 of infusion pump 10 when cassette 34 is loaded in the pump. Tubing 32 may additionally include upstream tubing 32A coming from a source of infusion liquid (not shown) and connected to an inflow end of tubing segment 32B, and downstream tubing 32C connected to an outflow end of tubing segment 32B and leading to a patient (not shown). Tubing segment 32B may be made of a different material than upstream tubing 32A and downstream tubing 32C, wherein the material of tubing segment 32B is chosen to have desired elasticity and flow parameters when engaged by pumping mechanism 12. For example, tubing segment 32B may be made of soft PVC or silicone, and tubing 32A, 32C may be standard PVC administration set tubing.

In addition to tubing segment 32B, cassette 34 comprises a cassette body 36 which may be monolithic. As used herein, the term "monolithic" means molded as a single homogenous piece or additively manufactured as a single homogenous piece. Cassette body 36 may be molded or additively manufactured, for example by three-dimensional printing, as a monolithic plastic part. By way of non-limiting example, cassette body 36 may be molded from a polycarbonate or TRITAN™ brand plastic.

Figure 5:
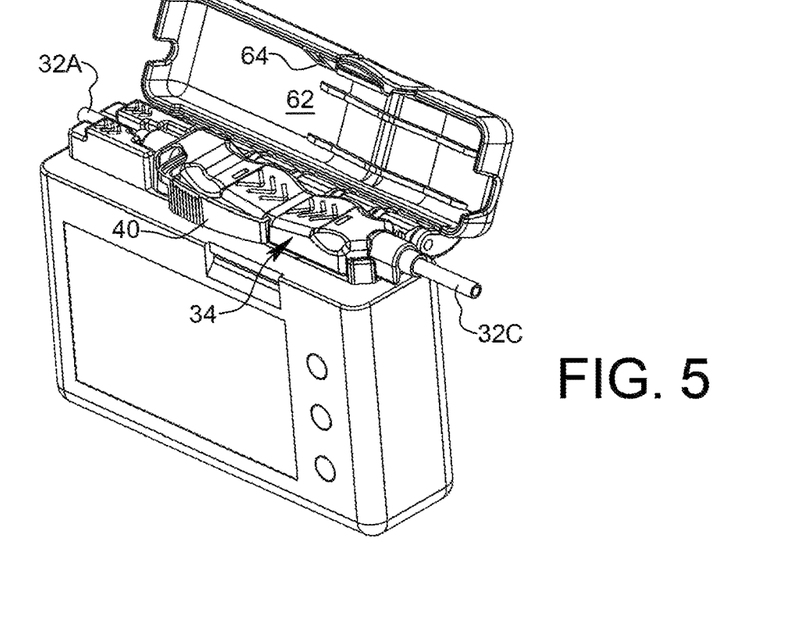
FIG. 5 is a perspective view showing the cassette loaded in the infusion pump prior to closure of a door of the pump.

Cassette body 36 may comprise a free-flow protection device 37 integrally formed as part of the monolithic cassette body. In the depicted embodiment, the free-flow-protection device 37 includes a fixed pinch element 38 and a pinch arm 40 having a movable pinch element 42. Pinch arm 40 normally resides in a closed position, illustrated in FIGS. 3A and 3B, in which movable pinch element 42 cooperates with fixed pinch element 38 to deform tubing segment 32B to stop the flow of liquid through the tubing segment. Pinch arm 40 is resiliently deflectable away from the closed position to an open position, illustrated in FIGS. 4A and 4B, in which movable pinch element 42 is positioned relative to fixed pinch element 38 such that the flow of liquid through tubing segment 32B is permitted, wherein deflection of pinch arm 40 away from the closed position spring biases the pinch arm toward the closed position. Free-flow protection device 37 and infusion pump 10 may be configured to cooperate with one another such that when cassette 34 is properly loaded into infusion pump 10, pinch arm 40 is deflected from the closed position to the open position. For example, pump 10 may include a cassette interface 60 (FIG. 1) configured for removably receiving cassette 34, and a door 62 movable relative to cassette interface 60 between a loading position depicted in FIG. 5 and a pumping position in which the door is closed and covers the cassette. In the illustrated embodiment, cassette 34 is placed into cassette interface 60 as shown in FIG. 5 such that tubing segment 32B of cassette 34 faces pumping mechanism 12 and may be operatively engaged by the pumping mechanism, and door 62 is closed over cassette 34 such that a cam surface 64 on door 62 engages pinch arm 40 and deflects the pinch arm from its closed position (FIGS. 3A and 3B) to its open position (FIGS. 4A and 4B), whereby flow through tubing segment 32B is permitted.

Cassette body 36 includes a platen surface 44 for stabilizing a side of tubing segment 32B opposite pumping mechanism 12 so that displacement of pumping fingers 22 toward platen surface 44 will resiliently deform tubing segment 32B to peristaltically move liquid through the tubing segment. At least a portion of tubing segment 32B extends adjacent to the convex platen surface 44 along a non-linear path determined by the convex platen surface. Cassette body 36 may include at least one grip 50 for holding tubing segment 32B adjacent to platen surface 44. For example, first and second grips 50 may be arranged near opposite ends of the platen surface 44, respectively.

Figure 6:
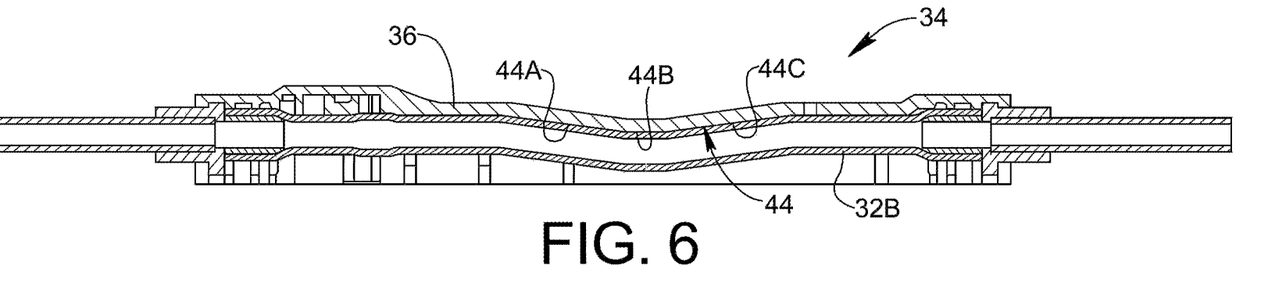
FIG. 6 is a cross-sectional view of the cassette taken generally along the line VI-VI in FIG. 4A.

As best seen in FIGS. 6 and 7, platen surface 44 is convex toward tubing segment 32B. For example, in the illustrated embodiment, platen surface 44 may have a trapezoidal profile and may include an inclined upstream surface region 44A, an inclined downstream surface region 44C, and a flat intermediate surface region 44B extending between upstream surface region 44A and downstream surface region 44C, wherein tubing segment 32B follows the trapezoidal profile of convex platen surface 44. The trapezoidal profile of platen surface 44 may be configured as an isosceles trapezoidal profile, i.e. upstream surface region 44A and downstream surface region 44C may be symmetrical about intermediate surface region 44B. Upstream surface region 44A may be longer than intermediate surface region 44B in an axial direction of tubing segment 32B. Likewise, downstream surface region 44C may be longer than intermediate surface region 44B in an axial direction of tubing segment 32B. In the illustrated embodiment, upstream surface region 44A and downstream surface region 44C form respective reflex angles of approximately 188° with intermediate surface region 44B in the trapezoidal profile. However, platen surface 44 may be configured with other reflex angle values between adjacent surface regions, and the reflex angle formed between upstream surface region 44A and intermediate surface region 44B need not be equal to the reflex angle formed between intermediate surface region 44B and downstream surface region 44C.

Figure 8:
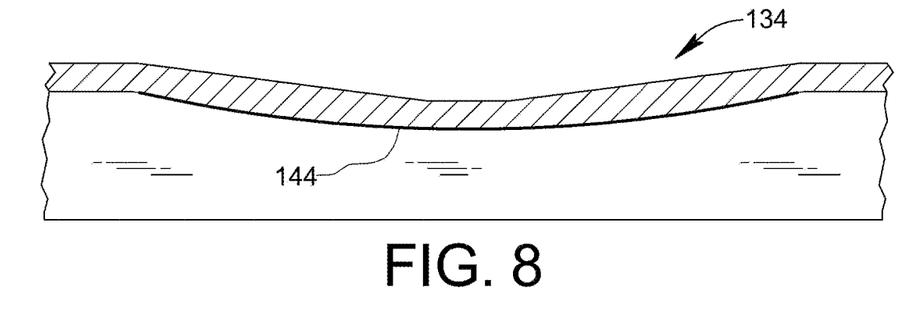
FIG. 8 is a cross-sectional view showing another possible configuration of the cassette platen surface in accordance with an alternative embodiment of the present disclosure.

FIG. 8 shows a cassette 134 including a cassette platen surface 144 having a convexly curved profile in accordance with an alternative embodiment of the present disclosure. Curved platen surface 144 may have an arc-shaped profile defined by a constant radius of curvature, or curved platen surface 144 may have a blended curve profile including multiple curve portions defined by different radii of curvature.

Figure 9:
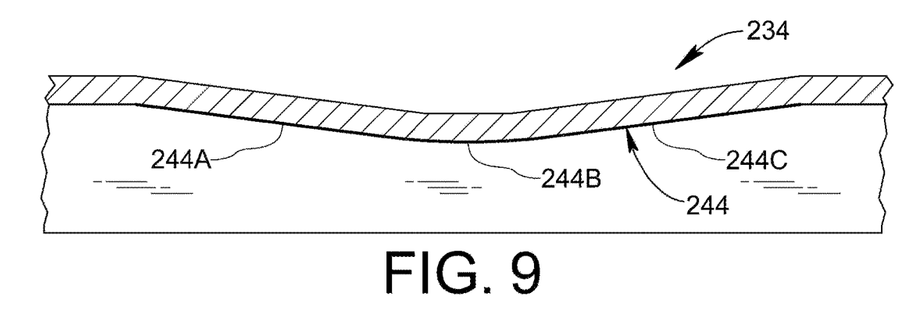
FIG. 9 is a view similar to that of FIG. 8, showing yet another possible configuration of the cassette platen surface in accordance with a further alternative embodiment of the present disclosure.

FIG. 9 shows a cassette 234 including a cassette platen surface 244 having a hybrid convex configuration in accordance with a further embodiment of the present disclosure. Convex platen surface 244 may include an upstream surface region 244A and a downstream surface region 244C each having an inclined linear profile, and an intermediate surface region 244B having a curved profile. As may be seen, intermediate surface region 244B extends between and connects upstream surface region 244A and downstream surface region 244C. Similar to the trapezoidal profile described above with reference to FIGS. 6 and 7, the profiles of upstream surface region 244A and downstream surface region 244C may be symmetrical about intermediate surface region 244B. Upstream surface region 244A may be longer than intermediate surface region 244B in an axial direction of tubing segment 32B. Likewise, downstream surface region 244C may be longer than intermediate surface region 244B in an axial direction of tubing segment 32B.

Figure 10:
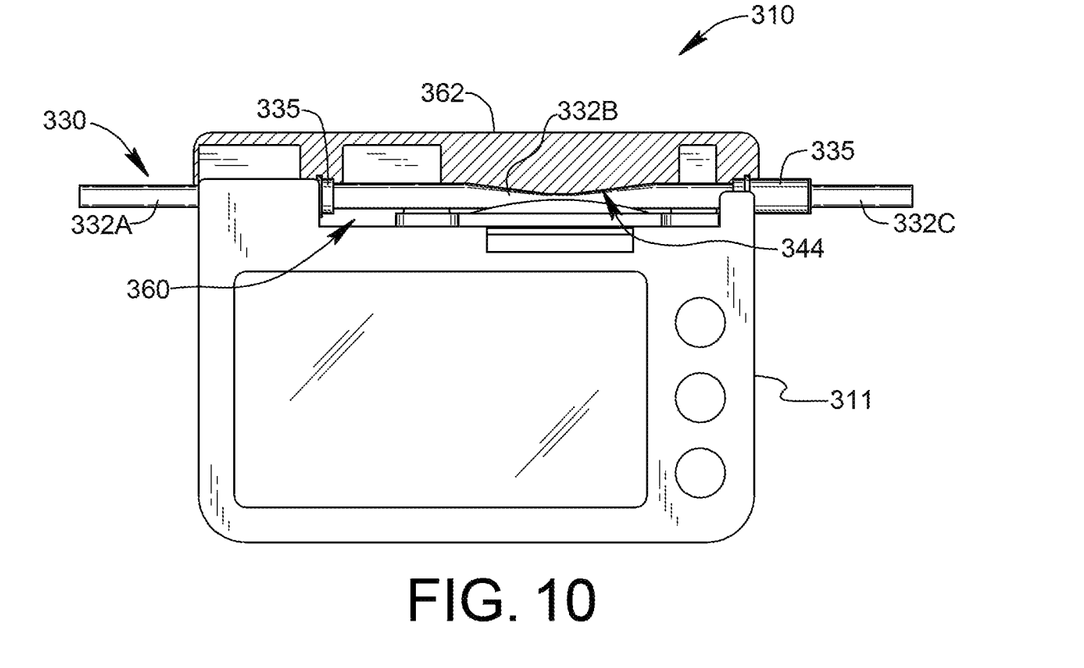
FIG. 10 is a partially-sectioned front view of an infusion pump having a convex platen surface in accordance with another embodiment of the present disclosure.

In the embodiments described above, the convex platen surfaces 44, 144, and 244 are formed as part of a cassette provided as part of a disposable administration set. FIG. 10 shows another embodiment of the present disclosure wherein a convex platen surface 344 is provided as part of an infusion pump 310.

Infusion pump 310 may be similar to infusion pump 10 described above in that it includes a peristaltic pumping mechanism. Infusion pump 310 is configured to receive and locate tubing of an administration set 330 operative engagement with the pumping mechanism of pump 310. Administration set 330 is illustrated as having a tubing segment 332B acted upon by the pumping mechanism, upstream tubing 332A coming from a source of infusion liquid (not shown) and connected to an inflow end of tubing segment 332B by a flanged connector 335, and downstream tubing 332C connected to an outflow end of tubing segment 332B by another flanged connector 335 and leading to a patient (not shown). Tubing segment 332B may be made of a different material than upstream tubing 332A and downstream tubing 332C, wherein the material of tubing segment 332B is chosen to have desired elasticity and flow parameters when engaged by the pumping mechanism of pump 310. For example, tubing segment 332B may be made of soft PVC or silicone, and tubing 332A, 332C may be standard PVC administration set tubing.

Pump 310 may include a tubing interface 360 configured for removably receiving administration set 330. For example, pump interface 360 may include recesses receiving flanged connectors 335 to locate tubing segment 332B over the pumping mechanism of pump 310. A door 362 may be hinged to a main body 311 of pump 310 for closure over pump interface 360 and the loaded portion administration set 330. In FIG. 10, hinged door 362 is sectioned to reveal the profile of platen surface 344, which may be provided on an underside of door 362. The profile of convex platen surface 344 may be similar to the profile of convex platen surface 44, convex platen surface 144, or convex platen surface 244 described above.

As best understood from FIGS. 7 and 11, use of a convex platen surface according to the present disclosure may be accompanied by a novel configuration of the pumping mechanism 12. As described above, the pumping mechanism 12 includes parallel pumping fingers 22 and cams 20 respectively associated with the parallel pumping fingers 22, wherein the cams are coupled to drive shaft 18 for rotation about a cam axis defined by the rotational axis of drive shaft 18 to cyclically drive the pumping fingers 22 into engagement with the tubing segment (the engagement may be indirect by virtue of a flexible fluid seal arranged overtop the ends of the pumping fingers 22). The plurality of cams 20 may include a pair of end cams 20A, 20C and at least one intermediate cam 20B between the pair of end cams 20A, 20C, wherein each of the pair of end cams 20A, 20C has a cam stroke which is greater than a cam stroke of each intermediate cam 20B. In the context of the present specification, "cam stroke" refers to a total linear displacement in a direction toward tubing segment 32B or 332B imparted by a cam 20 to an associated pumping finger 22 by rotation of the cam. For example, where cams 20 are circular cams having an eccentric axis of rotation spaced from the geometric center of the cam by an eccentricity distance, the cam stroke is twice the eccentricity distance. The cam stroke corresponding to each cam 20 may be designed to account for the particular profile of convex the platen surface 44, 144, 244, 344 and the location of the cam along the platen surface profile.

The improvements described in the present disclosure increase pumping efficiency relative to a linear peristaltic pump because the convex platen surface allows for a longer tubing segment for the same pumping mechanism length, whereby each pumping finger stroke pumps a greater volume of liquid. Moreover, one or both of the end cams 20A and 20C may be configured independently of intermediate cams 20B to actuate its respective associated pumping finger 22 in the manner of a compensating finger to reduce the no-flow and back-suction regions of the pumping cycle.

While the present disclosure describes exemplary embodiments, the detailed description is not intended to limit the scope of the appended claims to the particular embodiments set forth. The claims are intended to cover such alternatives, modifications and equivalents of the described embodiments as may be included within the scope of the claims.

What is claimed is:

1. A cassette for use with a pump for delivering liquid to a patient, the pump including a pumping mechanism having at least three pumping fingers and at least three cams rotatable about a cam axis to respectively actuate the at least three pumping fingers, the cassette comprising:

a cassette body loadable in the pump, the cassette body including a platen surface having a convex surface portion having an upstream surface region, an intermediate surface region, and a downstream surface region; and a segment of resiliently deformable tubing mounted to the cassette body for conveying a flow of liquid, at least a portion of the tubing segment extending adjacent to the convex surface portion along a non-linear path determined by the convex surface portion;

wherein the upstream surface region, the intermediate surface region, and the downstream surface region are arranged sequentially in a flow direction of liquid delivered through the segment of tubing, and the intermediate surface region connects the upstream surface region and the downstream surface region;

wherein, when the cassette is loaded into the pump, a distance between the convex surface portion and the cam axis decreases along the upstream surface region in the flow direction;

wherein, when the cassette is loaded into the pump, the distance between the convex surface portion and the cam axis does not increase along the intermediate surface region in the flow direction;

wherein, when the cassette is loaded into the pump, the distance between the convex surface portion and the cam axis increases along the downstream surface region in the flow direction; and wherein, when the cassette is loaded into the pump, the upstream surface region is opposite a first pumping finger of the at least three pumping fingers, the intermediate surface region is opposite a second pumping finger of the at least three pumping fingers, and the downstream surface region is opposite a third pumping finger of the at least three pumping fingers.

2. The cassette according to claim 1, wherein the convex surface portion has a trapezoidal profile, and wherein the tubing segment follows the trapezoidal profile of the convex surface portion.

3. The cassette according to claim 2, wherein the upstream surface region and the downstream surface region are symmetrical about the intermediate surface region.

4. The cassette according to claim 2, wherein the upstream surface region is longer than the intermediate surface region in an axial direction of the tubing segment.

5. The cassette according to claim 2, wherein the downstream surface region is longer than the intermediate surface region in an axial direction of the tubing segment.

6. The cassette according to claim 1, wherein the convex surface portion has a curved profile.

7. The cassette according to claim 1, wherein the upstream surface region and the downstream surface region each have an inclined linear profile, and the intermediate surface region has a curved profile.

8. An apparatus for delivering liquid to a patient, the apparatus comprising:
a segment of resiliently deformable tubing for conveying a flow of liquid in a flow direction,
a platen surface including a convex surface portion, the convex surface portion having an upstream surface region, an intermediate surface region, and a downstream surface region, wherein the upstream surface region, the intermediate surface region, and the downstream surface region are arranged sequentially in the flow direction, and the intermediate surface region connects the upstream surface region and the downstream surface region; and
a peristaltic pumping mechanism having at least three pumping fingers and at least three cams rotatable about a cam axis to respectively actuate the at least three pumping fingers, wherein the at least three fingers are opposite the convex surface portion;
wherein at least a portion of the tubing segment extends adjacent to the convex surface portion along a non-linear path determined by the convex surface portion and is arranged between the convex surface portion and the at least three pumping fingers for engagement by the at least three pumping fingers;

wherein a distance between the convex surface portion and the cam axis decreases along the upstream surface region in the flow direction;

wherein the distance between the convex surface portion and the cam axis does not increase along the intermediate surface region in the flow direction;

wherein the distance between the convex surface portion and the cam axis increases along the downstream surface region in the flow direction; and wherein the upstream surface region is opposite a first pumping finger of the at least three pumping fingers, the intermediate surface region is opposite a second pumping finger of the at least three pumping fingers, and the downstream surface region is opposite a third pumping finger of the at least three pumping fingers.

9. The apparatus according to claim 8, wherein the convex surface portion has a trapezoidal profile, and wherein the tubing segment follows the trapezoidal profile of the convex surface portion.

10. The apparatus according to claim 9, wherein the upstream surface region and the downstream surface region are symmetrical about the intermediate surface region.

11. The apparatus according to claim 9, wherein the upstream surface region is longer than the intermediate surface region in an axial direction of the tubing segment.

12. The apparatus according to claim 9, wherein the downstream surface region is longer than the intermediate surface region in an axial direction of the tubing segment.

13. The apparatus according to claim 8, wherein the convex surface portion has a curved profile.

14. The apparatus according to claim 8, wherein the upstream surface region and the downstream surface region each have an inclined linear profile, and the intermediate surface region has a curved profile.

15. The apparatus according to claim 8, wherein the pumping mechanism and the platen surface are structural components of an infusion pump.

16. The apparatus according to claim 8, wherein the pumping mechanism is a structural component of an infusion pump, and the platen surface is a structural component of a cassette loadable in the infusion pump.

17. The apparatus according to claim 16, wherein the tubing segment is a structural component of the cassette.

18. An apparatus for delivering liquid to a patient, the apparatus comprising:
a segment of resiliently deformable tubing for conveying a flow of liquid in a flow direction,
a platen surface including a convex surface portion, the convex surface portion having an upstream surface region, an intermediate surface region, and a downstream surface region, wherein the upstream surface region, the intermediate surface region, and the downstream surface region are arranged sequentially in the flow direction, and the intermediate surface region connects the upstream surface region and the downstream surface region; and
a peristaltic pumping mechanism having at least three pumping fingers and at least three cams rotatable about a cam axis to respectively actuate the at least three pumping fingers, wherein the at least three fingers are opposite the convex surface portion;
wherein at least a portion of the tubing segment extends adjacent to the convex surface portion along a non-linear path determined by the convex surface portion and is arranged between the convex surface portion and the at least three pumping fingers for engagement by the at least three pumping fingers;

wherein a distance between the convex surface portion and the cam axis decreases along the upstream surface region in the flow direction;

wherein the distance between the convex surface portion and the cam axis does not increase along the intermediate surface region in the flow direction;

wherein the distance between the convex surface portion and the cam axis increases along the downstream surface region in the flow direction; and wherein the upstream surface region is opposite a first pumping finger of the at least three pumping fingers, the intermediate surface region is opposite a second pumping finger of the at least three pumping fingers, and the downstream surface region is opposite a third pumping finger of the at least three pumping fingers; and wherein the at least three cams are coupled to a drive shaft for rotation about the cam axis to cyclically drive the at least three pumping fingers into engagement with the tubing segment, the at least three cams including a pair of end cams and at least one intermediate cam between the pair of end cams, wherein at least one of the pair of end cams has a cam stroke greater than a cam stroke of each intermediate cam.

19. The apparatus according to claim 18, wherein each of the pair of end cams has a cam stroke greater than a cam stroke of each intermediate cam.

* * * * *